US011478300B2

(12) United States Patent
Wang et al.

(10) Patent No.: US 11,478,300 B2
(45) Date of Patent: Oct. 25, 2022

(54) ABLATION ELECTRODE ASSEMBLY AND METHODS FOR IMPROVED CONTROL OF TEMPERATURE AND MINIMIZATION OF COAGULATION AND TISSUE DAMAGE

(71) Applicant: St. Jude Medical, Atrial Fibrillation Division, Inc., St. Paul, MN (US)

(72) Inventors: Huisun Wang, Maple Grove, MN (US); Jeremy D. Dando, Plymouth, MN (US); Dale E. Just, Minneapolis, MN (US); Allen P. Moore, Brooklyn Park, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 216 days.

(21) Appl. No.: 16/678,475

(22) Filed: Nov. 8, 2019

(65) Prior Publication Data
US 2020/0129232 A1 Apr. 30, 2020

Related U.S. Application Data

(60) Division of application No. 15/413,024, filed on Jan. 23, 2017, now Pat. No. 10,499,985, which is a
(Continued)

(51) Int. Cl.
*A61B 18/14* (2006.01)
*A61B 34/20* (2016.01)
*A61B 18/00* (2006.01)

(52) U.S. Cl.
CPC .......... *A61B 18/1492* (2013.01); *A61B 2018/00095* (2013.01); *A61B 2018/00101* (2013.01);
(Continued)

(58) Field of Classification Search
CPC ...... A61B 18/1492; A61B 2018/00095; A61B 2018/00101; A61B 2034/2051;
(Continued)

(56) References Cited

U.S. PATENT DOCUMENTS 3,331,371 A * 7/1967 Rocchi ............ A61M 25/10185
604/99.04
3,671,979 A 6/1972 Moulopoulos
(Continued)

FOREIGN PATENT DOCUMENTS

EP 2 019 640 A2 2/2009
JP H09140801 A 6/1997
(Continued)

OTHER PUBLICATIONS

Wittkampf, Fred H., Radiofrequency ablation with a colled porous electrode catheter, JACC vol. II, No. 2; 17a (Feb. 1988).
(Continued)

*Primary Examiner* — Michael F Peffley
(74) *Attorney, Agent, or Firm* — Armstrong Teasdale LLP

(57) ABSTRACT

The present invention pertains to multiple piece irrigated ablation electrode assemblies wherein the irrigation channels are insulated or separated from at least one temperature sensing mechanism within the distal portion of the electrode assembly. The present invention further pertains to methods for improved assembly and accurate measurement and control of the electrode temperatures while effectively irrigating the device and target areas.

15 Claims, 8 Drawing Sheets

Related U.S. Application Data division of application No. 14/821,054, filed on Aug. 7, 2015, now Pat. No. 9,549,777, which is a continuation of application No. 11/953,615, filed on Dec. 10, 2007, now abandoned, which is a continuation-in-part of application No. 11/948,362, filed on Nov. 30, 2007, now Pat. No. 8,128,621, which is a continuation-in-part of application No. 11/434,220, filed on May 16, 2006, now Pat. No. 7,857,810.

(52) U.S. Cl.
CPC ............ *A61B 2018/00577* (2013.01); *A61B 2018/00791* (2013.01); *A61B 2034/2051* (2016.02); *A61B 2218/002* (2013.01)

(58) Field of Classification Search
CPC ........... A61B 2018/00791; A61B 2018/00577; A61B 2218/002
See application file for complete search history.

(56) References Cited

U.S. PATENT DOCUMENTS

| | | | |
|---|---|---|---|
| 4,026,298 A | 5/1977 | Grausz | |
| 4,084,606 A | 4/1978 | Mittleman | |
| 4,841,984 A | 6/1989 | Armeniades et al. | |
| 4,857,054 A | 8/1989 | Helfer | |
| 5,056,517 A | 10/1991 | Fenici | |
| 5,061,823 A | 10/1991 | Carroll | |
| 5,092,844 A | 3/1992 | Schwartz et al. | |
| 5,098,431 A * | 3/1992 | Rydell | A61B 18/1492 606/48 |
| 5,112,301 A | 5/1992 | Fenton et al. | |
| 5,122,137 A * | 6/1992 | Lennox | A61B 18/1206 606/40 |
| 5,230,349 A | 7/1993 | Langberg | |
| 5,290,263 A | 3/1994 | Wigness et al. | |
| 5,334,193 A * | 8/1994 | Nardella | A61B 18/1492 606/41 |
| 5,348,554 A * | 9/1994 | Imran | A61B 18/1492 606/41 |
| 5,403,276 A | 4/1995 | Schechter et al. | |
| 5,423,811 A | 6/1995 | Imran et al. | |
| 5,427,114 A | 6/1995 | Colliver et al. | |
| 5,456,682 A * | 10/1995 | Edwards | A61B 18/00 600/549 |
| 5,462,521 A * | 10/1995 | Brucker | A61M 25/0082 604/20 |
| 5,545,161 A * | 8/1996 | Imran | A61B 18/1492 606/41 |
| 5,643,197 A | 7/1997 | Brucker et al. | |
| 5,660,205 A | 8/1997 | Epstein | |
| 5,688,267 A * | 11/1997 | Panescu | A61B 18/1492 606/31 |
| 5,697,927 A | 12/1997 | Imran et al. | |
| 5,755,760 A * | 5/1998 | Maguire | A61M 25/0138 607/122 |
| 5,779,669 A * | 7/1998 | Haissaguerre | A61M 25/0041 604/95.01 |
| 5,792,140 A | 8/1998 | Tu et al. | |
| 5,800,428 A * | 9/1998 | Nelson | A61B 18/1492 606/41 |
| 5,843,152 A | 12/1998 | Tu et al. | |
| 5,893,885 A * | 4/1999 | Webster, Jr. | A61B 18/1492 607/122 |
| 5,913,856 A * | 6/1999 | Chia | A61B 18/1492 606/41 |
| 5,951,546 A * | 9/1999 | Lorentzen | A61B 18/1482 606/41 |
| 5,957,961 A * | 9/1999 | Maguire | A61B 18/1492 607/99 |
| 5,961,513 A * | 10/1999 | Swanson | A61B 18/1492 606/34 |
| 5,971,968 A | 10/1999 | Tu et al. | |
| 5,989,249 A | 11/1999 | Kirwan | |
| 6,017,338 A | 1/2000 | Brucker et al. | |
| 6,044,845 A | 4/2000 | Lewis | |
| 6,050,986 A | 4/2000 | Hektner | |
| 6,080,151 A | 6/2000 | Swartz et al. | |
| 6,120,500 A | 9/2000 | Bednarek et al. | |
| 6,171,275 B1 * | 1/2001 | Webster, Jr. | A61B 18/1492 604/20 |
| 6,210,406 B1 | 4/2001 | Webster | |
| 6,217,573 B1 | 4/2001 | Webster | |
| 6,217,576 B1 | 4/2001 | Tu et al. | |
| 6,241,724 B1 | 6/2001 | Fleischman et al. | |
| 6,322,558 B1 | 11/2001 | Taylor et al. | |
| 6,356,790 B1 * | 3/2002 | Maguire | A61M 25/0147 607/102 |
| 6,405,078 B1 * | 6/2002 | Moaddeb | A61N 1/06 604/113 |
| 6,425,894 B1 | 7/2002 | Brucker et al. | |
| 6,475,214 B1 * | 11/2002 | Moaddeb | A61B 18/1492 606/41 |
| 6,506,189 B1 * | 1/2003 | Rittman, III | A61B 18/1482 606/41 |
| 6,575,969 B1 | 6/2003 | Rittman et al. | |
| 6,602,242 B1 | 8/2003 | Fung et al. | |
| 6,611,699 B2 * | 8/2003 | Messing | A61B 18/1492 606/49 |
| 6,628,976 B1 * | 9/2003 | Fuimaono | A61M 25/0147 600/374 |
| 6,650,923 B1 | 11/2003 | Lesh et al. | |
| 6,659,959 B2 | 12/2003 | Brockway et al. | |
| 6,662,034 B2 | 12/2003 | Segner et al. | |
| 6,757,565 B2 * | 6/2004 | Sharkey | A61B 18/148 607/101 |
| 6,770,070 B1 | 8/2004 | Balbierz | |
| 6,852,120 B1 * | 2/2005 | Fuimaono | A61B 18/1482 |
| 6,926,669 B1 * | 8/2005 | Stewart | A61B 18/1492 600/437 |
| 6,955,675 B2 | 10/2005 | Jain | |
| 6,977,469 B2 | 12/2005 | Seinen et al. | |
| 6,984,232 B2 | 1/2006 | Vanney et al. | |
| 7,025,742 B2 | 4/2006 | Rubenstein et al. | |
| 7,166,105 B2 | 1/2007 | Mulier et al. | |
| 7,311,708 B2 * | 12/2007 | McClurken | A61B 18/1492 606/50 |
| 7,591,816 B2 | 9/2009 | Wang et al. | |
| 7,815,635 B2 * | 10/2010 | Wittkampf | A61B 18/1492 606/41 |
| 7,824,406 B2 | 11/2010 | Wang et al. | |
| 7,857,810 B2 | 12/2010 | Wang et al. | |
| 7,951,143 B2 | 5/2011 | Wang et al. | |
| 8,052,684 B2 | 11/2011 | Wang | |
| 8,128,621 B2 | 3/2012 | Wang | |
| 8,287,533 B2 * | 10/2012 | Wittkampf | A61B 18/1492 606/49 |
| 8,394,093 B2 | 3/2013 | Wang | |
| 8,690,870 B2 | 4/2014 | Wang et al. | |
| 9,433,760 B2 * | 9/2016 | Subramaniam | A61B 18/1492 606/49 |
| 9,468,494 B2 * | 10/2016 | O'Sullivan | A61B 18/1492 606/50 |
| 9,549,777 B2 * | 1/2017 | Wang | A61B 18/1492 606/49 |
| 10,182,734 B2 * | 1/2019 | O'Sullivan | A61M 25/0082 604/20 |
| 10,653,479 B2 * | 5/2020 | O'Sullivan | A61B 18/1492 606/48 |
| 2002/0026188 A1 | 2/2002 | Babierz et al. | |
| 2002/0058866 A1 | 5/2002 | Segner | |
| 2002/0058933 A1 | 5/2002 | Christopherson et al. | |
| 2002/0120261 A1 | 8/2002 | Morris et al. | |
| 2002/0177846 A1 | 11/2002 | Mulier et al. | |
| 2003/0004506 A1 | 1/2003 | Messing | |
| 2003/0014035 A1 | 1/2003 | Trombley, III et al. | |
| 2003/0060822 A1 * | 3/2003 | Schaer | A61B 18/1492 606/41 |
| 2003/0069549 A1 | 4/2003 | MacMahon et al. | |
| 2003/0199867 A1 | 10/2003 | Wellman | |

(56) References Cited

U.S. PATENT DOCUMENTS

| | | |
|---|---|---|
| 2003/0225364 A1 | 12/2003 | Kraft |
| 2004/0030279 A1 | 2/2004 | Rubenstein et al. |
| 2004/0054272 A1 | 3/2004 | Messing |
| 2004/0098022 A1 | 5/2004 | Barone |
| 2004/0102825 A1 | 5/2004 | Daoud |
| 2004/0176801 A1 | 9/2004 | Edwards et al. |
| 2004/0243121 A1 | 12/2004 | Lee |
| 2004/0267106 A1 | 12/2004 | Segner et al. |
| 2005/0015082 A1* | 1/2005 | O'Sullivan ............. B29C 33/52 606/41 |
| 2005/0049453 A1 | 3/2005 | Faulkner |
| 2005/0070894 A1 | 3/2005 | McClurken |
| 2005/0085769 A1 | 4/2005 | MacMahon |
| 2005/0137659 A1 | 6/2005 | Garabedian et al. |
| 2005/0143798 A1 | 6/2005 | Bleam et al. |
| 2005/0149116 A1 | 7/2005 | Edwards et al. |
| 2005/0177151 A1 | 8/2005 | Coen et al. |
| 2005/0209580 A1 | 9/2005 | Freyman |
| 2005/0256521 A1 | 11/2005 | Kozel |
| 2005/0267467 A1 | 12/2005 | Paul et al. |
| 2005/0273006 A1 | 12/2005 | Stewart et al. |
| 2005/0288654 A1 | 12/2005 | Nieman et al. |
| 2006/0036303 A1 | 2/2006 | Schwartz |
| 2006/0058775 A1 | 3/2006 | Stevens et al. |
| 2006/0058854 A1 | 3/2006 | Abrams et al. |
| 2006/0089638 A1 | 4/2006 | Carmel et al. |
| 2006/0106298 A1* | 5/2006 | Ahmed ................. A61B 5/062 600/381 |
| 2006/0229599 A1 | 10/2006 | Rashidi |
| 2006/0278248 A1 | 12/2006 | Viswanathan |
| 2006/0287650 A1 | 12/2006 | Cao et al. |
| 2007/0270791 A1* | 11/2007 | Wang ................... A61B 18/148 606/41 |
| 2008/0045943 A1* | 2/2008 | Wittkampf ......... A61B 18/1492 606/41 |
| 2008/0071267 A1* | 3/2008 | Wang ................. A61B 18/1492 606/41 |
| 2008/0091193 A1 | 4/2008 | Kauphusman et al. |
| 2008/0161794 A1 | 7/2008 | Wang |
| 2009/0143779 A1* | 6/2009 | Wang ................. A61B 18/1492 606/41 |
| 2009/0163911 A1* | 6/2009 | Cao ................... A61B 18/1492 606/41 |
| 2016/0008059 A1* | 1/2016 | Prutchi .............. A61B 18/1492 606/41 |
| 2017/0027641 A1* | 2/2017 | O'Sullivan ........ A61B 18/1492 604/20 |

FOREIGN PATENT DOCUMENTS

| | | | |
|---|---|---|---|
| JP | 2002065692 A | 3/2002 | |
| JP | 2009545338 A | 12/2009 | |
| WO | WO 95/05771 A1 | 3/1995 | |
| WO | WO 96/37146 A1 | 11/1996 | |
| WO | WO 1996/036860 A2 | 11/1996 | |
| WO | WO-9926546 A1 * | 6/1999 | ......... A61B 18/1402 |
| WO | WO 1999/056812 A2 | 11/1999 | |
| WO | WO 2001/03589 A1 | 1/2001 | |
| WO | WO 2005/048858 A1 | 6/2005 | |
| WO | WO 2005/112814 A2 | 12/2005 | |
| WO | WO 2006/007305 A2 | 1/2006 | |
| WO | WO 2007/136979 A2 | 11/2007 | |
| WO | WO 2008/010039 A2 | 1/2008 | |
| WO | WO 2008/045925 A2 | 4/2008 | |
| WO | WO 2009/023385 A1 | 2/2009 | |
| WO | WO 2009/070448 a1 | 6/2009 | |
| WO | WO 2009/152151 A1 | 12/2009 | |

OTHER PUBLICATIONS

Wittkampf, Fred. Saline-Irrigated Radiofrequency ablation electrode with external cooling. Journal of Cardiovascular Electrophysiology, vol. 16, No. 3 (Mar. 2005) pp. 323-328.

Soejima, K. Saline-Cooled Versus Standard Radiofrequency Catheter Ablation for Infarct-Related Ventricular Tachycardias. Circulation, vol. 103, pp. 1858-1862 (Apr. 10, 2001).

Yokoyama, K. Comparison of Electrode Cooling Between Internal and Open Irrigation in Radiofrequency Ablation Lesion Depth and Incidence of Thrombus and Steam Pop, Circulation, vol. 113. pp. 11-19 (Jan. 3-10, 2006).

Jais, Pierre. Prospective Randomized Comparison of Irrigated Tip Versus Conventional Tip Catheter for Ablation of Common Flutter. Circulation, vol. 101, pp. 772-776, (Feb. 22, 2000).

Nakagawa, H. Inverse Relationship Between Electrode Size and Lesion Size During Radiofrequency Ablation With Active Electrode Cooling., vol. 98, pp. 458-465, (Aug. 4, 1998).

Yamane, Teiichi. Efficacy and Safety of an Irrigated-Tip Catheter for the Ablation of Accessory Pathways Resistant to Conventional Radiofrequency Ablation. vol. 102. pp. 2565-2568 (Nov. 21, 2000).

Weiss, Christian. Radiofrequency Catheter Ablation Using Cooled Electrodes: Impact of Irrigation Flow Rate and Catheter Contact Pressure on Lesion Dimensions. PACE, vol. 25, No. 4, pp. 463-469 (Apr. 2002).

"Medical Design with Sterile Piezo Motor Technology." PI Medical. N.p., Web. Feb. 20, 2013. <http://www.pi-medical.net/index.php>.

"Piezoelectric Micropump." Takasago Fluid Systems. N.p., n.d. Web. Jun. 11, 2013.http://www.takasago-fluidics.com/products_pump/piezo.

\* cited by examiner

ABLATION ELECTRODE ASSEMBLY AND METHODS FOR IMPROVED CONTROL OF TEMPERATURE AND MINIMIZATION OF COAGULATION AND TISSUE DAMAGE

CROSS-REFERENCE TO RELATED APPLICATIONS

The present application is a divisional of U.S. application Ser. No. 15/413,024 (the '024 application), filed 23 Jan. 2017, presently pending now U.S. patent application Ser. No. 10,499,985, which is a divisional of U.S. application Ser. No. 14/821,054 (the '054 application), filed 7 Aug. 2015, now U.S. Pat. No. 9,549,777, which is a continuation of U.S. application Ser. No. 11/953,615 (the '615 application), filed 10 Dec. 2007, abandoned, which is a continuation-in-part of U.S. application Ser. No. 11/948,362 (the '362 application), filed 30 Nov. 2007, now U.S. Pat. No. 8,128,621, which is a continuation-in-part of U.S. application Ser. No. 11/434,220 (the '220 application), filed 16 May 2006, now U.S. Pat. No. 7,857,810. This application is related to U.S. application Ser. No. 11/646,237 (the '237 application), now U.S. Pat. No. 7,824,406, U.S. application Ser. No. 11/646,255 (the '255 application), now U.S. Pat. No. 7,951,143, U.S. application Ser. No. 11/646,275 (the '275 application), now U.S. Pat. No. 8,690,870, and U.S. application Ser. No. 11/646,270 (the '270 application), now U.S. Pat. No. 7,591,816, all filed on Dec. 28, 2006. The '024 application, the '054 application, the '615 application, the '362 application, the '220 application, the '237 application, the '255 application, the '275 application, and the '270 application are all hereby incorporated by reference in their entirety as though fully set forth herein.

BACKGROUND OF THE INVENTION a. Field of the Invention

The present invention pertains generally to ablation electrode assemblies. More particularly, the present invention is directed toward ablation electrode assemblies for use in the human body having at least one temperature sensing device and a mechanism for irrigating the ablation assembly and targeted areas. The present invention also relates to methods for improved assembly and accurate measurement and control of the electrode temperatures while effectively irrigating the device and target areas.

b. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

Because RF ablation may generate significant heat, which if not carefully monitored and/or controlled can result in protein denaturation, blood coagulation, excess tissue damage, such as steam pop, tissue charring, and the like, it is desirable to monitor the temperature of the ablation assembly. It is further desirable to include a mechanism to irrigate the target area and the device with biocompatible fluids, such as saline solution. This irrigation mitigates excess, unwanted tissue damage and mitigates rising temperatures from the electrode assembly, which potentially causes premature shutdown of the ablative assembly during operation. However, introduction of this irrigation solution may inhibit the ability to accurately monitor and/or control the temperature of the ablation assembly during use.

There are typically two classes of irrigated electrode catheters, open and closed irrigation catheters. Closed ablation catheters typically circulate a cooling fluid within the inner cavity of the electrode. Open ablation catheters, on the other hand, typically deliver the cooling fluid through open orifices on the electrode. Examples of these known catheters include the THERMOCOOL brand of catheters marketed and sold by Biosense-Webster. The current open irrigated ablation catheters use the inner cavity of the electrode, or distal member, as a manifold to distribute saline solution. The saline thus flows directly through the open orifices of the distal electrode member. This direct flow through the distal electrode tip lowers the temperature of the distal tip during operation, rendering accurate monitoring and control of the ablative process more difficult.

In these open electrode irrigated catheters, it has been determined that insulating the irrigation channels from the ablation electrode is beneficial. One such example was published on or around March 2005 in an article entitled "Saline-Irrigated Radiofrequency Ablation Electrode with Electrode Cooling," by Drs. Wittkampf and Nakagawa, et al., the content of which is hereby incorporated by reference in its entirety. Similarly, the content of PCT International Publication No. WO 05/048858, published on Jun. 2, 2005, is hereby incorporated by reference in its entirety.

BRIEF SUMMARY OF THE INVENTION

The present invention provides for significant improvements over known irrigation catheters, including those disclosed by Drs. Wittkampf and Nakagawa, et al., by providing a multiple piece irrigated ablation electrode assembly that provides the advantages of irrigating the target area and the electrode assembly while simultaneously improving the operation, temperature response, temperature monitoring and/or control mechanisms of the ablation assembly, so as to prevent unwanted, unnecessary tissue damage. The present invention further provides for ablation electrode assemblies that are easier to manufacture and assemble than known irrigated ablation electrode assemblies.

The present invention is directed to improved irrigated ablation electrode assemblies and methods useful in conjunction with irrigated catheter and pump assemblies and RF generator assemblies designed to monitor and control the ablation process while minimizing blood coagulation and unnecessary tissue damage.

The present invention provides for an irrigated ablation electrode assembly for use with an irrigated catheter device comprising a proximal member having at least one passageway for a fluid and at least one outlet for the fluid; and a distal member having at least one temperature sensor located within the distal member, wherein the passageway and the at least one outlet are spaced from the at least one temperature sensor by at least a portion of a poor thermally conductive material.

In one embodiment, the proximal member is comprised of a poor thermally conductive material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof. The distal member is comprised of an electrically, and potentially thermally, conductive material selected from the group consisting of platinum, gold, iridium, palladium, stainless steel, and mixtures thereof.

In another embodiment, the proximal member and the distal member are comprised of an electrically, and potentially thermally, conductive material selected from the group consisting of platinum, gold, iridium, palladium, stainless steel, and mixtures thereof. The material for the proximal member need not be the same as the distal member. In this embodiment, the distal member and the proximal member are separated by a poor thermally conductive material and are electrically connected though an electrical connection device. The proximal member is then electrically connected to an electrical source through an electrical connection device.

The present invention further includes an irrigated ablation electrode assembly comprising an electrode member comprising at least one temperature sensor; and an irrigation member having at least one conduit for a fluid, the at least one conduit being thermally insulated from the distal member.

In one embodiment, the irrigation member is comprised of a poor thermally conductive material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof. The electrode member is comprised of an electrically, and potentially thermally, conductive material selected from the group consisting of platinum, gold, iridium, stainless steel, and mixtures thereof.

In another embodiment, the irrigation and electrode members are comprised of an electrically, and potentially thermally, conductive material selected from the group consisting of platinum, gold, iridium, palladium, stainless steel, and mixtures thereof, but they need not be comprised of the same material. In this embodiment, the electrode member and the irrigation member are separated by a poor thermally conductive material and are electrically connected though an electrical connection device. The irrigation member is then electrically connected to an electrical source through an electrical connection device.

In accordance with embodiments of the present invention, the at least one passageway or conduit of the proximal or irrigation member extends at either an angle substantially perpendicular to a horizontal, i.e., longitudinal, axis of the proximal or irrigation member, or axially towards the distal member at an angle substantially less than perpendicular to a longitudinal axis of the proximal or irrigation member, between approximately 15 and 70 degrees, preferably approximately 30 to 45 degrees, most preferably approximately 30 degrees.

Further, the ablation electrode assembly may also include a second and, optionally, a third poor thermally conductive material disposed between the proximal or irrigation member and the distal or electrode member selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof. The ablation electrode assembly may also include a second and, optionally, a third thermally conductive material disposed between the temperature sensor(s) and the distal or electrode member.

The present invention further includes methods for improved measurement and control of a temperature of an irrigated ablation electrode assembly or a target site and minimization of coagulation and excess tissue damage at and around the target site comprising the following steps: providing an ablation electrode assembly having at least one temperature sensor disposed within a distal or electrode member of the irrigated electrode assembly and having a proximal or irrigation member separate from the distal member; providing an irrigation pathway within the proximal member for delivery of a fluid to an external portion of the ablation electrode assembly and the target site to minimize excess tissue damage during operation of the ablation electrode assembly; providing a poor thermally conductive material between the irrigation pathway and the distal member to accurately measure the temperature of the distal member during operation of the ablation electrode and during delivery of the fluid to the target site. The methods further include the step of providing a second and, optionally, a third poor thermally conductive material disposed between the irrigation pathway and the distal member. The methods also include the step of providing a thermally conductive material between the at least one temperature sensor and the distal member.

Additional methods for improved measurement and control of a temperature of an irrigated ablation electrode assembly or a target site and minimization of coagulation and excess tissue damage at and around the target site during operation comprise the following steps: obtaining an ablation electrode having at least one temperature sensor disposed with a distal member and a passageway for distribution of a fluid to the target site, the passageway being insulated from the temperature sensor; irrigating the target site during operation of the ablation electrode by passing the fluid through the passageway; monitoring the temperature sensor(s) during operation of the ablation electrode; and maintaining operational parameters so as to minimize excess tissue damage during operation of the ablation electrode. The methods further contemplate delivering the fluid to an outer portion of the distal member.

Further methods for improved assembly of irrigation electrode assemblies are provided comprising the following steps: providing a distal member having at least one locking member extending from an inner portion of an open end of the distal member and extending a predetermined length angularly outward from the open end and terminating in a lip extending toward the central axis of the distal member; providing a proximal member having at least one locking member extending from an inner portion of an open end of the distal member extending a predetermined length angularly outwardly from the open end, terminating in a lip extending toward the central axis of the distal member; and pressing the distal member and the proximal member together. These methods may also include the step of providing a poor thermally conductive adhesive between the proximal member and the distal member, whereby when the proximal member and the distal member are pressed together, a further chemical bond is achieved.

A technical advantage of the present invention is that the electrode assembly thermally separates the cooling irrigation fluid from the distal member, and more particularly the temperature sensing mechanism(s) within the distal member, thereby allowing for improved temperature control and/or monitoring while simultaneously allowing for irrigation of the electrode assembly and the target areas to minimize coagulation and unwanted tissue damage. The separation of the cooling fluid from the temperature sensing mechanisms further allows for better monitoring of rising temperature of the electrode assembly during operation, as well as other tell-tale factors of over-ablation of targeted tissue areas.

Another advantage of the present invention is improved manufacturability of insulated, irrigated ablation electrode assemblies. The multiple piece design of the ablation electrode assembly allows for ease of manufacture and assembly of ablation electrode catheters over known electrode assemblies.

Yet another advantage of the invention is the ability to easily manufacture and assemble any number of known sizes of irrigated electrode assemblies, including 2 mm, 2½ mm and 4 mm assemblies.

The foregoing and other aspects, features, details, utilities, and advantages of the present invention will be apparent from reading the following description and claims, and from reviewing the accompanying drawings.

DETAILED DESCRIPTION OF EXEMPLARY EMBODIMENTS

Figure 1:
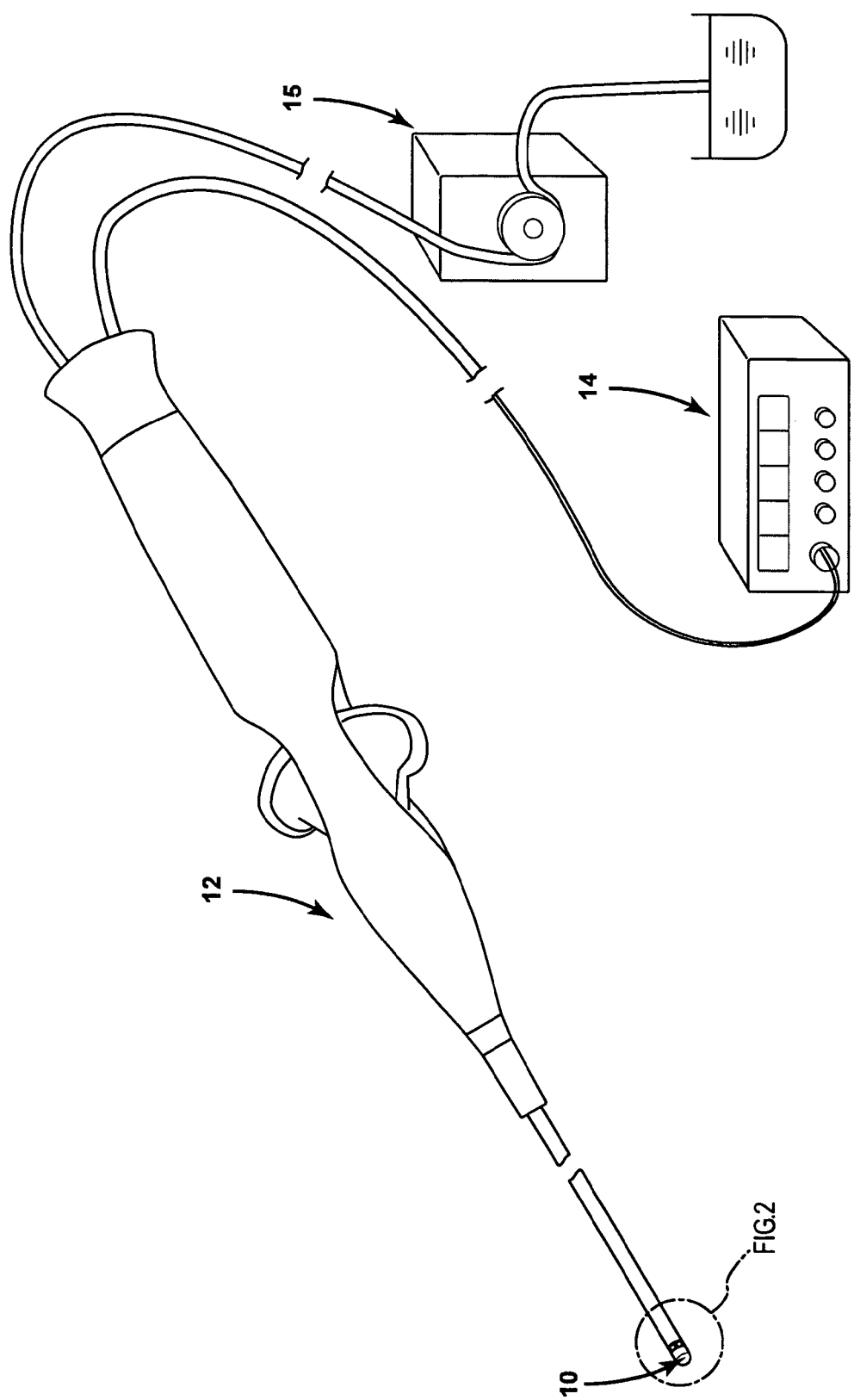
FIG. 1 is an isometric view of an ablation electrode assembly 10 according to a first embodiment of the present invention in conjunction with an irrigated catheter assembly 12 operably connected to an RF generator assembly 14 and a pump assembly 15.

In general, the instant invention relates to irrigated ablation electrode assemblies 10, 11, 13, 19, 21, and 23, and to methods of manufacturing and using such irrigated ablation electrode assemblies. For purposes of this description, similar aspects among the various embodiments described herein will be referred to by the same reference number. As will be appreciated, however, the structure of the various aspects may be different among the various embodiments.

The ablation electrode assembly may comprise part of an irrigated ablation catheter 12 assembly, operably connected to a pump assembly 15 and a RF generator assembly 14 which serves to facilitate the operation of ablation procedures through monitoring any number of chosen variables (e.g., temperature of the ablation electrode, ablation energy, and position of the assembly), assist in manipulation of the assembly during use, and provide the requisite energy source delivered to the electrode assembly 10. The present embodiments describe RF ablation electrode assemblies and methods, but it is contemplated that the present invention is equally applicable to any number of other ablation electrode assemblies where the temperature of the device and the targeted tissue areas is a factor during the procedure.

FIG. 1 is a general perspective view of an irrigated ablation catheter assembly having a RF generator assembly 14 and a fluid pump assembly 15 operably connected to an irrigation catheter 12 assembly having an irrigated electrode assembly 10 according to the present invention operably attached thereto. The structural and functional features of the catheter assembly 12 and the RF generator assembly 14 and pump assembly 15 are well-known to those of skill in the art. For example, the RF generator assembly could be an IBI-1500T RF Cardiac Ablation Generator available from Irvine Biomedical, Inc. in Irvine, Calif. 92614. The RF generator assembly could also be any other known assembly, including, for example, a Stockert RF generator available from Biosense, or one of the Atakr® series of RF generators available from Medtronic. The pump assembly can be any known assembly, including fixed volume rolling pumps, variable volume syringe pumps, and any other pump assembly known to those of skill in the art. FIGS. 2-8, discussed in more detail below, exemplify various embodiments of the irrigated ablation electrode assembly 10 according to the present invention.

Figure 2:
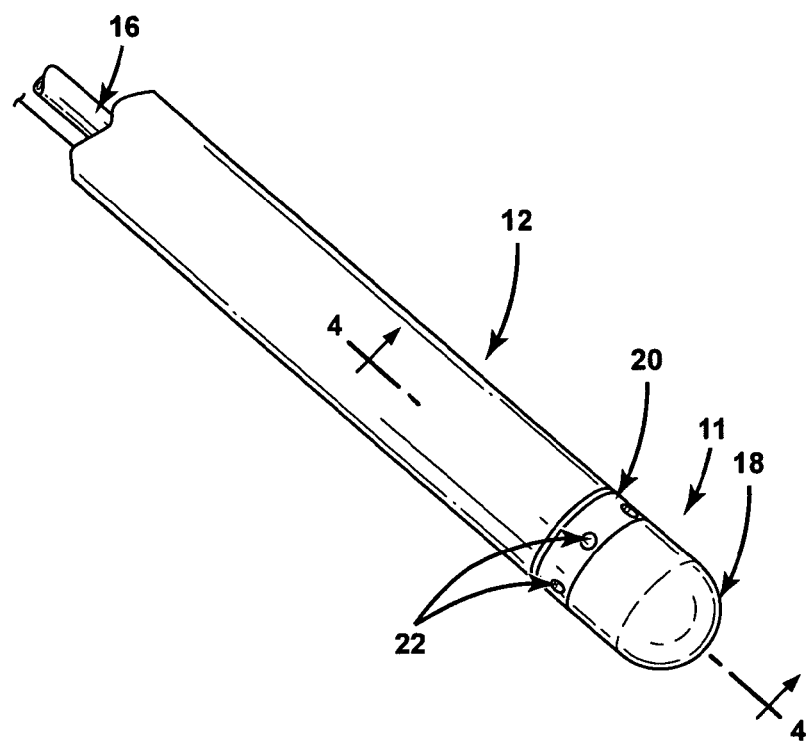
FIG. 2 is an enlarged, isometric view of the ablation electrode assembly 11 according to the first embodiment of the present invention operably connected to an irrigated catheter assembly 12.

FIG. 2 is an isometric view of an ablation electrode assembly 11 connected to an irrigated ablation catheter assembly 12 having a fluid delivery tube 16 therein. The ablation electrode assembly 11 generally comprises an irrigation member 20 and an ablation electrode assembly 18. The orientation of the member 20 and assembly 18 are generally such that the ablation electrode assembly 18 is situated at the distal end of the assembly with the irrigation member 20 located at the proximal end of the assembly, although it is conceivable the orientation could be reversed. The proximal member 20 has at least one passageway 24 (not shown) and at least one outlet 22 for delivery of a fluid to targeted tissue areas and the outside of the electrode assembly 11. The distal member 18 further comprises at least one temperature sensing mechanism 26 (not shown) disposed therein and operably connected to the RF generator assembly 14. The distal member 18 is comprised of any electrically, and potentially thermally, conductive material known to those of ordinary skill in the art for delivery of ablative energy to target tissue areas. Examples of the thermally conductive material include gold, platinum, iridium, palladium, stainless steel, and any mixtures thereof. Moreover, there are a number of electrode designs contemplated within the scope of the present invention including tip electrodes, ring electrodes, and any combination thereof.

In general accordance with the embodiments described herein, the fluid passageway(s) 24 and outlet(s) 22 are separated from the distal member 18, and accordingly the temperature sensing mechanism 26, by at least one poor thermally conductive material. A poor thermally conductive material is one with physical attributes that decreases heat transfer from the passageway(s) 24 to the distal member 18 by about 10% or more, and more preferably by about 25% or more measured by known methods to one of ordinary skill in the art. In particular embodiments, materials that decreased heat transfer by more than approximately 75% performed favorably. It is further contemplated that a poor thermally conductive material could have physical attributes that decrease heat transfer less than about 10%, provided that the remaining structural components are selected with the appropriate characteristics and sensitivities to maintain adequate monitoring and control of the process. Thus, while these properties are preferred, the poor thermally conductive material may be any material known to one of skill in the art consistent with the spirit of the invention. Examples of poor thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof.

As shown in more detail with respect to specific embodiments below, the poor thermally conductive material may be the material comprising the proximal member 20, or the distal member 18, a separate material from the proximal member 20 and the distal member 18, or any combination thereof. Additionally, the passageway(s) 24 and outlet(s) 22 defined by the proximal member 18 may also be separated longitudinally from the end 46 of the distal member 18 thereby providing the benefit of insulating the passageway(s) 24 from the temperature sensor(s) 26 for improved temperature monitoring of the ablated target area during operation. The poor thermally conductive material, and the separation from the end 46 of the distal member 18, serve individually, and cooperatively, to minimize the effect of the lower temperature of the fluid delivered through the passageway(s) 24 and outlet(s) 22 from the temperature sensing mechanism(s) 26 within the distal member 18. The separation of the passageway(s) 24 and outlet(s) 22 from the distal member 18, and more particularly the temperature sensing mechanism 26 to facilitate the dual purposes of (1) effectively irrigating the electrode assembly 10 and the targeted tissue area to minimize coagulation and unwanted tissue damage and (2) effectively controlling the operation of the ablation electrode assembly 10 in accordance with objects of the present invention.

Figure 3:
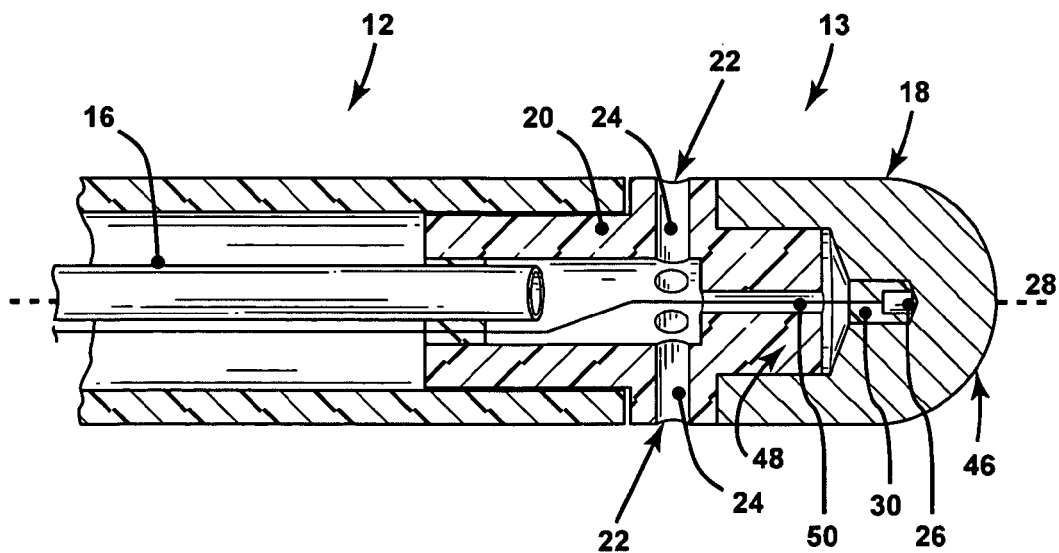
FIG. 3 is a cross-sectional view of an ablation electrode assembly 13 according to a second embodiment of the present invention.
Figure 5:
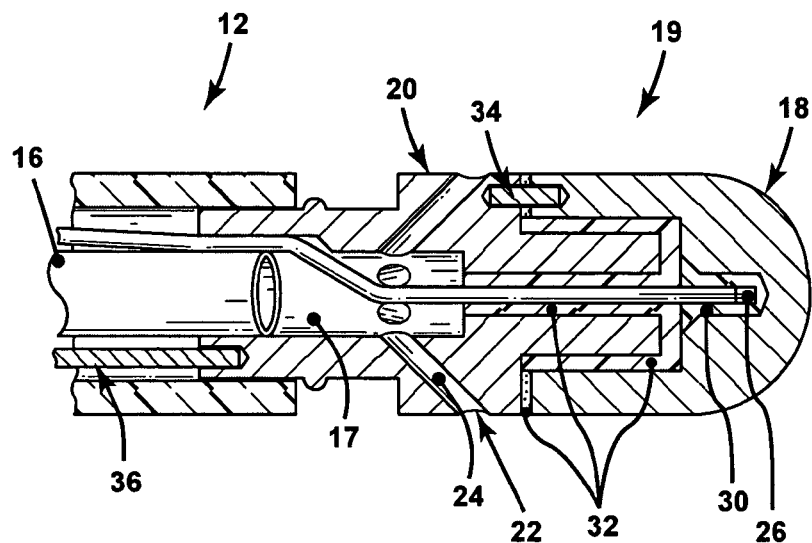
FIG. 5 is a cross-sectional view similar to FIGS. 3 and 4 of an ablation electrode assembly 19 according to a third embodiment of the present invention.
Figure 6:
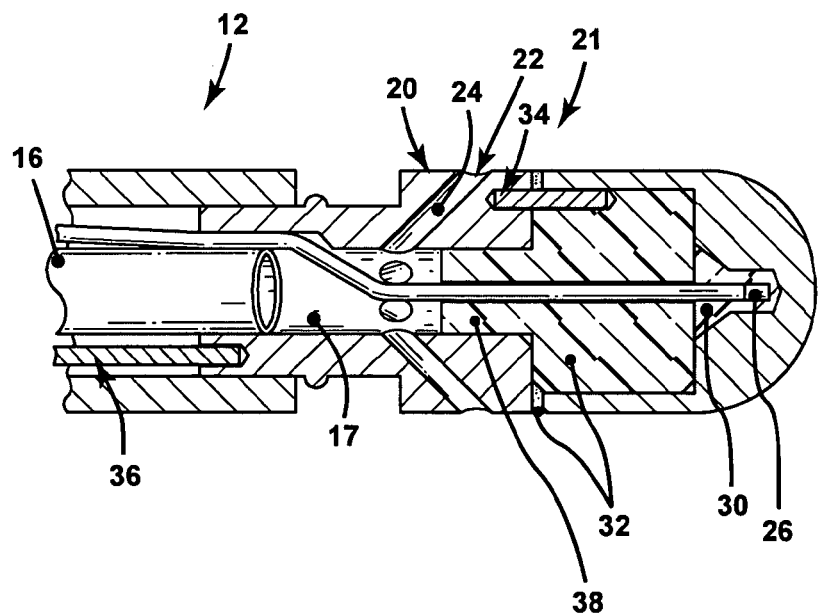
FIG. 6 is a cross-sectional view similar to FIGS. 3-5 according to a fourth embodiment of the present invention.

FIG. 3 is a cross-sectional view of an embodiment of the ablation electrode assembly 13. FIG. 3 describes what is known to those in the art as a 2½ mm (length) ablation electrode assembly 10. A 2½ mm ablation electrode assembly 10 is often beneficial because it requires less power (around 10-20 W, as compared to around 20-40 W for a 4 mm assembly). However, it is contemplated that any size ablation electrode assembly 13, including a 4 mm assembly, is equally technically acceptable. In instances where a larger ablation area is desired to provide for different spatial orientation of the electrode assembly 13, for example as shown in FIGS. 5 and 6 below, a larger electrode surface area can be accommodated, while still yielding the desirable separation between the cooling passageways 24 and the temperature sensing mechanism 26.

As shown in FIG. 3, an ablation electrode assembly 13 is connected to an irrigation catheter assembly 12 having a fluid delivery tube 16. The ablation electrode assembly 13 comprises a proximal member 20, or manifold, a distal member 18, and a temperature sensing mechanism 26 operably connected to the RF generator assembly 14 (not shown). In this embodiment, the proximal member 20 itself is comprised of a poor thermally conducting material that serves to insulate the fluid from the remaining portions of the assembly 13. Preferably the proximal member 20 is made from a poor thermally conductive polymer, more preferably from a polyether ether ketone ("PEEK") because of this material's combination of thermal and physical properties. The proximal member 20 is configured to receive the fluid tube 16 of the catheter assembly 12 and comprises a plurality of passageways 24 extending from a central axis 28 of the assembly 13 axially toward the outer portion of the proximal member 20 terminating in corresponding outlets 22. Preferably, the plurality of passageways 24 are equally distributed around the proximal member 20 so as to provide equal distribution of fluid to the targeted tissue area and the outside of the assembly 13. The passageway 24 may be a single, annular passageway, or a number of individual passageways equally distributed around the proximal member 20. In this embodiment, the passageways 24 are at an angle substantially perpendicular to the horizontal axis 28 of the assembly 13. In operation, fluid is pumped through the delivery tube 16 and passes through the passageways 24 and through the outlets 22 where it contacts with targeted tissue areas and the outside portion of the ablation electrode assembly 13.

The proximal member 20 is further configured to extend a portion 48 into the distal member 18 and has a pathway 50 for passage of the operable connection of the temperature sensing mechanism 26 within the distal tip 18. In this embodiment, this path 50 is shown extending substantially through the middle of the proximal member 20, however, this path 50 can be located anywhere within or outside the proximal member 20. The resulting cross-sectional shape is substantially cross-shaped, in which the fluid passageways 24 and conduits 22 are isolated from other portions of the assembly 13 by the proximal member 20.

The distal member 18 of the ablation electrode assembly 13 has a generally cylindrical shape terminating in a semi-spherical end. The distal member 18 is configured to accept a portion 48 of the proximal member 20 for attachment thereto. The distal member 18 may be connected to the proximal member 20 by any known mechanism (not shown) including adhesives, press-fit configurations, snap-fit configurations, or any other mechanism known to one of skill in the art.

The distal member 18 further contains at least one temperature sensing mechanism 26 disposed therein for measurement and control of the assembly 13 and targeted tissue areas during operation. It is further contemplated that additional temperature sensing mechanisms (not shown) can be utilized for further control and monitoring of the temperature of the assembly 13 at various additional locations. For purposes of the present invention, the temperature sensing mechanism(s) 26 can be any mechanism known to one of skill in the art, including for example, thermocouples or thermistors. In a further embodiment, the temperature sensing mechanism 26 is surrounded, or encapsulated, by a second thermally conductive and electrically non-conductive material 30. This thermally conductive and electrically non-conductive material 30 serves to hold the temperature sensing mechanism 26 in place within the distal tip 18 and provides excellent heat exchange between the temperature sensing mechanism 26 and the distal member. This material 30 may be comprised of a number of materials known to one of skill in the art, including, for example, thermally conductive resins, epoxies, or potting compounds, such as the material sold under the trademark STYCAST 2651 MM.

Figure 4:
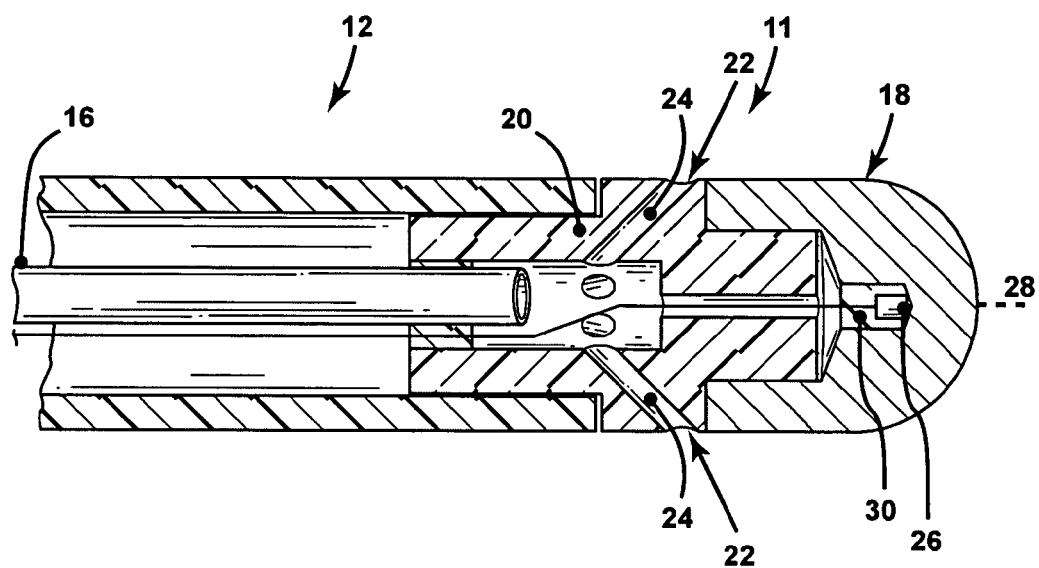
FIG. 4 is a cross-sectional view of the ablation electrode assembly 11 of FIG. 2 taken along line 4-4 of FIG. 2.

FIG. 4 is a cross-sectional view of another embodiment of the ablation electrode assembly 11, similar to that described above and shown in FIG. 3. In this embodiment, however, the fluid delivery conduits 24, or passageways, extend at an angle substantially less than perpendicular to the horizontal axis 23. Angling of the passageways 24 away from perpendicular, but less than parallel, further assists in the delivery of the fluid to the targeted tissue areas, further decreases the risk of coagulation of the bodily fluids during ablation procedures, and allows for improved measurement and control of the ablation assembly 11 during operation. Preferably, the passageways 24 extend at an angle between approximately 20 and 70 degrees, more preferably at an angle between approximately 30 and 60 degrees, and most preferably at an angle of approximately 30 degrees. It is also contemplated that the passageways may be further angled in a second dimension, such that the passageways and orifices are configured to provide fluid to the external portion of the assembly in a swirling, or helical fashion. This configuration serves to keep the fluid in closer proximity to the electrode assembly, thereby further preventing against coagulation during operation.

Again, in this embodiment, the temperature sensing mechanism 26 is surrounded, or encapsulated, by a second thermally conductive and electrically non-conductive material 30. This thermally conductive and electrically non-conductive material 30 serves to hold the temperature sensing mechanism 26 in place within the distal tip 28 and provides excellent heat exchange between the temperature sensing mechanism 26 and the distal member. This material 30 may be comprised of a number of materials known to one of skill in the art, including for example, thermally conductive resins, epoxies, or potting compounds, such as the material sold under the trademark STYCAST 2651 MM.

FIG. 5 is a cross-sectional view of yet another embodiment of the ablation electrode assembly according to the present invention. In accordance with this embodiment, the electrode assembly 19 comprises a distal member 18 configured to house at least one temperature sensing mechanism 26 (only one shown) and a proximal member 20 having a fluid delivery conduit 17, at least one passageway 24 and at least one orifice 22 for delivery of a fluid to target tissue areas and the outside of the ablation electrode assembly 19. The fluid delivery conduits 24, or passageways, extend axially away from the horizontal axis 28 of the assembly 19 at an angle of approximately 45 degrees from perpendicular. In preferred embodiments, an angle of 30 degrees also performed favorably. Such angled passageways 24 are preferred because they further decrease coagulation around the target tissue areas during operation. The proximal member 20 is configured to accept a fluid delivery tube 16 from an irrigation catheter 12 and is further configured to mate with the irrigation catheter assembly 12 and the fluid pump assembly 15. Consistent with the other embodiments, the proximal member 20 can be attached to the catheter assembly 12 by any known mechanism, including snap-fit, pressure fit, physically or chemically bonded, or any combination thereof.

In this embodiment, the proximal member 20 and the distal member 18 are both comprised of electrically, and possibly thermally, conductive materials. In this embodiment, both the proximal 20 and distal 18 members are electrically connected to an ablation power source (not shown) and are capable of ablating targeted tissue areas. The members may be made of the same material, or may be comprised of different materials.

The proximal member 20 and distal member 18 are separated from each other in this embodiment through at least one poor thermally conductive material 32. Additionally, the proximal member 20 and the distal member 18 may be bonded together using a thermally-poor conductive adhesive 32 known to those of skill in the art. In this instance, the proximal 20 and distal 18 members are electrically connected through any electrical connection device 34, such as an electrically conductive wire. The proximal member 20 is electrically connected to an energy source (not shown) through another electrical connection device 36. The result of this configuration provides the benefit of an increased ablation electrode surface area (encompassing both the distal and proximal members), where the proximal member 20 is generally cooler than the distal member 18. At least one temperature sensing mechanism 26 is placed within the distal member 18. The temperature sensing mechanism 26 may be further surrounded, or encapsulated, by another thermally conductive, electrically non-conductive, material 30. This thermally conductive, electrically non-conductive, material serves to hold the temperature sensing mechanism 26 in place within the distal tip 18 and provides excellent heat exchange between the temperature sensing mechanism 26 and the distal member. This material 30 may be comprised of a number of materials known to one of skill in the art, including for example, thermally conductive resins, epoxies, or potting compounds, such as the material sold under the trademark STYCAST 2651 MM. By placing the temperature sensing mechanism 26 within the distal member 18, displaced from the proximal member 20, improved temperature measurements and control are still maintained, while allowing for decreased coagulation and unnecessary tissue damage through irrigation. This particular configuration enables the use of a number of different sizes of ablation electrodes 10, including 4 mm electrodes, ring electrodes, and combinations thereof.

FIG. 6 is a cross-section view of yet another embodiment of the present invention, similar to that described above and shown in FIG. 5. In this embodiment, the distal member 18, or the proximal member 20 comprises another poor thermally conductive material 32 displaced between the proximal member 20 and the distal member 18. This additional poor thermally conductive material 32 provides further insulation of the temperature sensing mechanism(s) 26 thereby further allowing for improved temperature measurements and control of the ablation assembly 21, while allowing for decreased coagulation and unnecessary tissue damage through irrigation. Similar to the embodiment described above and shown in FIG. 5, the distal member 18 and proximal member 20 may be chemically bonded together with thermally poor conductive adhesives known to those in the art. In this instance, the distal member 18 and the proximal member 20 are electrically connected through an electrical connection device 34, such as a wire. In the instance where such an adhesive is not utilized, the electrical connection between the proximal 20 and distal 18 members is accomplished via direct contact.

Figure 7:
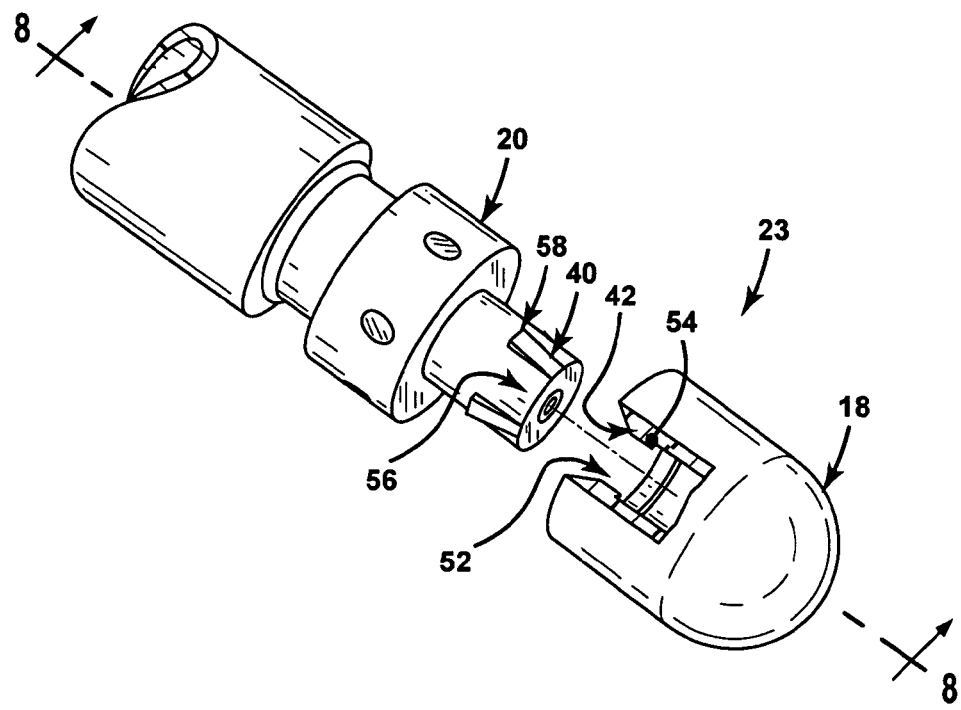
FIG. 7 is an isometric, exploded view of an ablation electrode assembly according to a fifth embodiment of the present invention.
Figure 8:
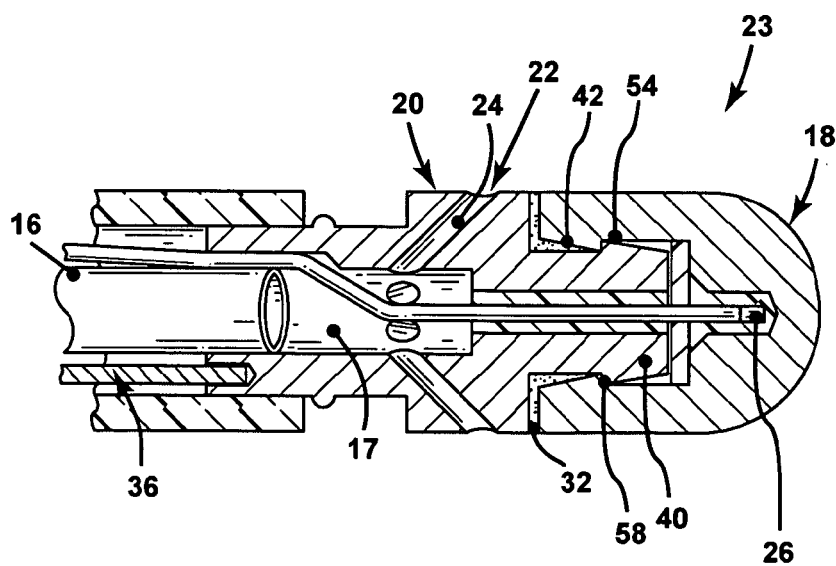
FIG. 8 is a cross-sectional view taken along line 8-8 of FIG. 7.

FIG. 7 is an isometric, exploded view of yet another embodiment of the present invention, similar to that described above and shown in FIGS. 5 and 6. In this embodiment, the distal member 18 and the proximal member 20 are cooperatively configured to facilitate a snap-fit, or pressure-fit connection assembly. As an example, the distal member 18 is configured with at least one locking member 42 extending from an inner portion 52 of the open end of the distal member 18 extending a predetermined length angularly outward from the open end, terminating in a lip 54 extending toward the central axis of the distal member 18. Cooperatively, the proximal end 20 has at least one locking member 40 extending from an inner portion 56 of the open end of the distal member 20 extending a predetermined length angularly outward from the open end, terminating in a lip 58 extending toward the central axis of the proximal member 20. FIG. 8 shows a cross-sectional view taken along section 8 of FIG. 7. When lined up and pressed together, the distal member 18 and the proximal members 20 thereby form a snap-fit assembly. In addition to the embodiment shown in FIG. 8, any number of locking members 40, 42 can be utilized, including both locking members 40, 42 having a single annular rib 54, 58 extending substantially around the inside of the member 40, 42. It is also contemplated that the locking lips 54, 58 could be eliminated to form a pressure-fit connection assembly. It is further contemplated that in addition to the mechanical assemblies, the distal 18 and proximal 20 members can be further chemically bonded with a poor thermally conductive adhesive 32 known to those of skill in the art. Utilizing such a configuration provides the additional benefit of eliminating the need for an electrical connection wire 34, while simultaneously allowing for additional insulation and strength of connection between the members 18, 20 through use of a poor thermally conductive adhesive 32, for the electrical connection is served by the touching of the lips 54, 58 of the respective members 18, 20.

In addition to the preferred embodiments discussed above, the present invention contemplates methods for improved measurement and control of a temperature of an irrigated ablation electrode assembly 23 or a target site and minimization of coagulation and excess tissue damage at and around the target site. According to one method, an ablation electrode assembly 23 is provided, having at least one temperature sensor 26 disposed within a distal member 18 of the irrigated electrode assembly 23 and having a proximal member 20 separate from the distal member 18. A separate irrigation pathway 24 is provided within the proximal member 20 for delivery of a cooling fluid to an external portion of the ablation electrode assembly 23 and the target site to minimize excess tissue damage during operation of the ablation electrode. A poor thermally conductive material is also provided between the irrigation pathway 24 within the distal member 18 thereby allowing for improved measurement of the temperature of the ablation electrode assembly 23 during operation, while simultaneously allowing for the benefits of irrigation of the target site and external portions of the electrode assembly 10, such as minimizing tissue damage, such as steam pop, preventing rising impedance of the ablation assembly, and minimizing blood coagulation. Additionally, a second, optionally a third, poor thermally conductive material 32 can be provided between the irrigation pathway 24 within the proximal member 20 and the temperature sensing mechanism 26 further enhancing the measurement and control of temperature of the electrode assembly while simultaneously allowing for the benefits of irrigation of the target site and external portions of the electrode assembly 23.

Another method for improved measurement and control of a temperature of an irrigated ablation electrode assembly 23 or a target site and minimization of coagulation and excess tissue damage at and around the target site during operation comprises the steps of obtaining an ablation electrode 10 having a temperature sensor 26 disposed with a distal member 18 and a passageway 24 for distribution of a fluid to the target site, the passageway 24 being insulated from the temperature sensor 26; irrigating the target site during operation of the ablation electrode by passing the fluid through the passageway 24; monitoring the temperature sensor 26 during operation of the ablation electrode 10; and maintaining operational parameters so as to minimize excess tissue damage during operation of the ablation electrode. This method further contemplates the step of delivering the fluid to an outer portion of the distal member 18.

The present invention further provides for yet additional improved methods of assembly of irrigation electrode assemblies 23, by providing distal member 18 and a proximal member 20 cooperatively configured to facilitate a snap-fit, or pressure-fit connection assembly. In accordance with this method, a distal member 18 is provided having at least one locking member 42 extending from an inner portion 52 of the open end of the distal member 18 extending a predetermined length angularly outward from the open end, terminating in a lip 54 extending toward the central axis of the distal member 18. Cooperatively, a proximal member 20 is provided having at least one locking member 40 extending from a portion 56 of the proximal member 20 extending a predetermined length angularly outward from the end 56, terminating in a lip 58 extending toward the central axis of the proximal member 20. The complete assembly 23 is configured by pressing the distal member 18 and the proximal member 20 together until they snap into place. Additionally, the contemplated methods further comprise providing a poor thermally conductive 32 adhesive between the proximal member 20 and the distal member 18, such that when snapped into place, a further chemical bond is achieved, that further insulates the fluid passageways 24 from the temperature sensing mechanism(s) 26 within the distal member 18.

EXAMPLES

Two designs in accordance with the present invention were prepared and tested against a design representative of known irrigated ablation catheters and a control design representative of known non-insulated irrigated ablation catheter.

Design A represents an irrigated electrode assembly 10 as shown in FIG. 3 having fluid passageways 24 configured substantially perpendicular to the horizontal axis of the manifold 20. The manifold 20 of Design A was made of PEEK, machined into the configuration described in FIG. 3. The distal member 18 was comprised of stainless steel and contained a single thermocouple 26 disposed therein encapsulated by STYCAST.

Design B represents an irrigated electrode assembly 10 similar in design to FIG. 4 having fluid passageways 24 configured at an angle of approximately 45 and 30 degrees from perpendicular to the horizontal axis of the manifold 20. The manifold 20 of Design A was made of PEEK, machined into the configuration described in FIG. 4. The distal member 18 was comprised of stainless steel and contained a single thermocouple 26 disposed therein encapsulated by STYCAST.

Design C represents a single piece irrigated electrode assembly having individually insulated irrigation pathways extending both axially and longitudinally to the distal tip. Design C was prepared in accordance with the insulated ablation electrode assembly disclosed in Drs. Wittkampf and Nakagawa's publication entitled "Saline-Irrigated Radiofrequency Ablation Electrode with Electrode Cooling" cited above, with the exception that the passageways extending axially from the horizontal axis of the assembly were not separately insulated. This resulted in an insulated ablation assembly in which approximately 85% of the irrigation pathways were insulated from the distal member. The pathways were insulated using PEEK tubing.

The Control design represents a non-insulated, single piece irrigated electrode assembly having irrigation pathways extending both axially and longitudinally to the distal tip. The structure of the distal member was prepared in accordance with the insulated ablation electrode assembly disclosed in Drs. Wittkampf and Nakagawa's publication entitled "Saline-Irrigated Radiofrequency Ablation Electrode with Electrode Cooling" cited above, without any corresponding insulation surrounding the individual cooling fluid passageways.

Bench tests were conducted on experimental fresh cow cardiac tissue tested in a 37 degree Celsius saline water bath for a period of 30 seconds and 60 seconds, using the various irrigated ablation catheter assemblies operating at 10 W, 100 ohms impedance, 80 degrees Celsius, and simulated circulatory conditions of from 0.125 L/min to 1 L/min. The saline solution was delivered with an adjustable syringe pump that allowed for varying flow rates of saline of from 8 ml/min to 16 ml/min. The temperature of the end of the distal member and the tissue temperature were monitored and plotted against time.

Figure 9:
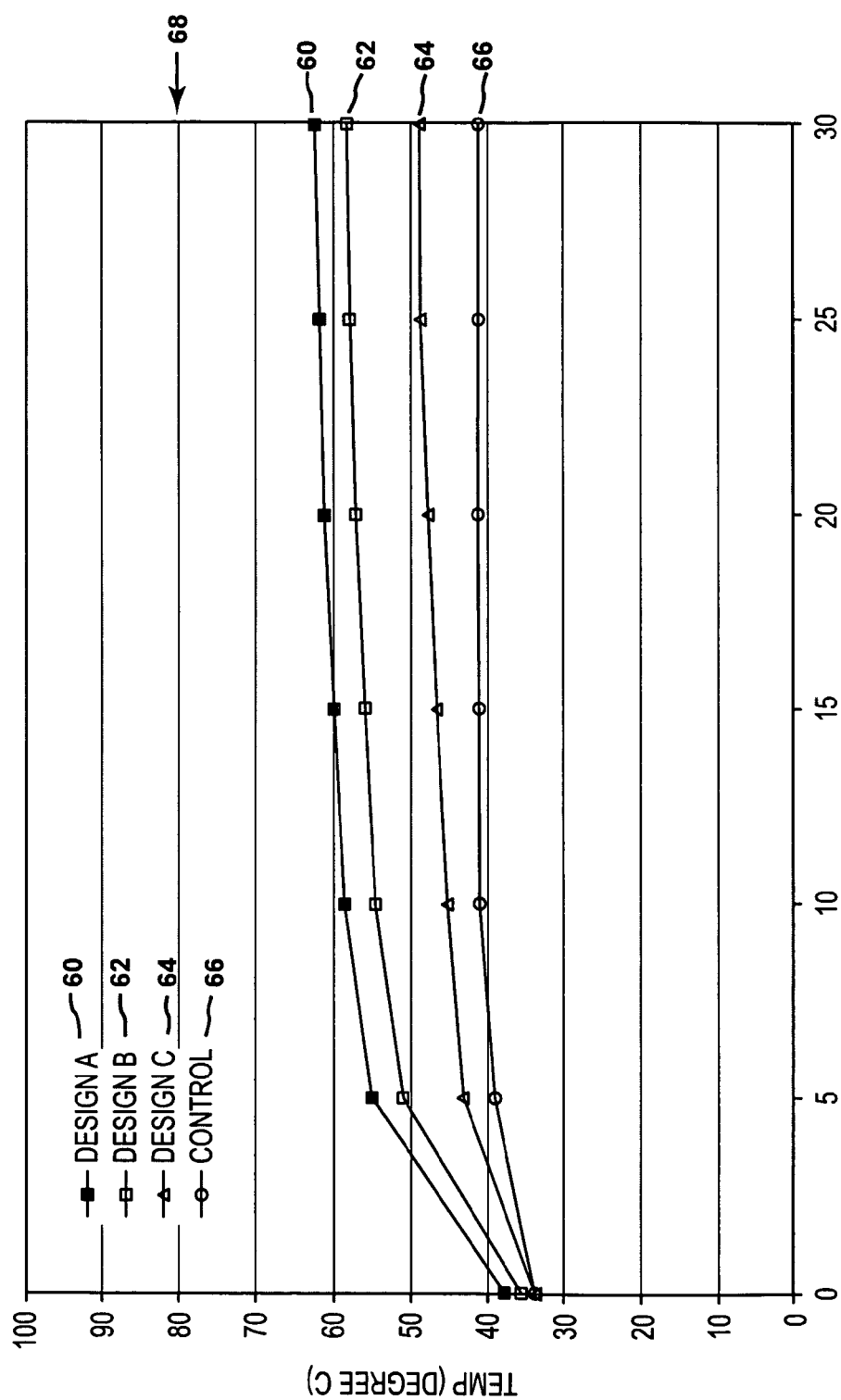
FIGS. 9, 10 and 11 graphically depict bench test results for ablation electrode assemblies.
Figure 10:
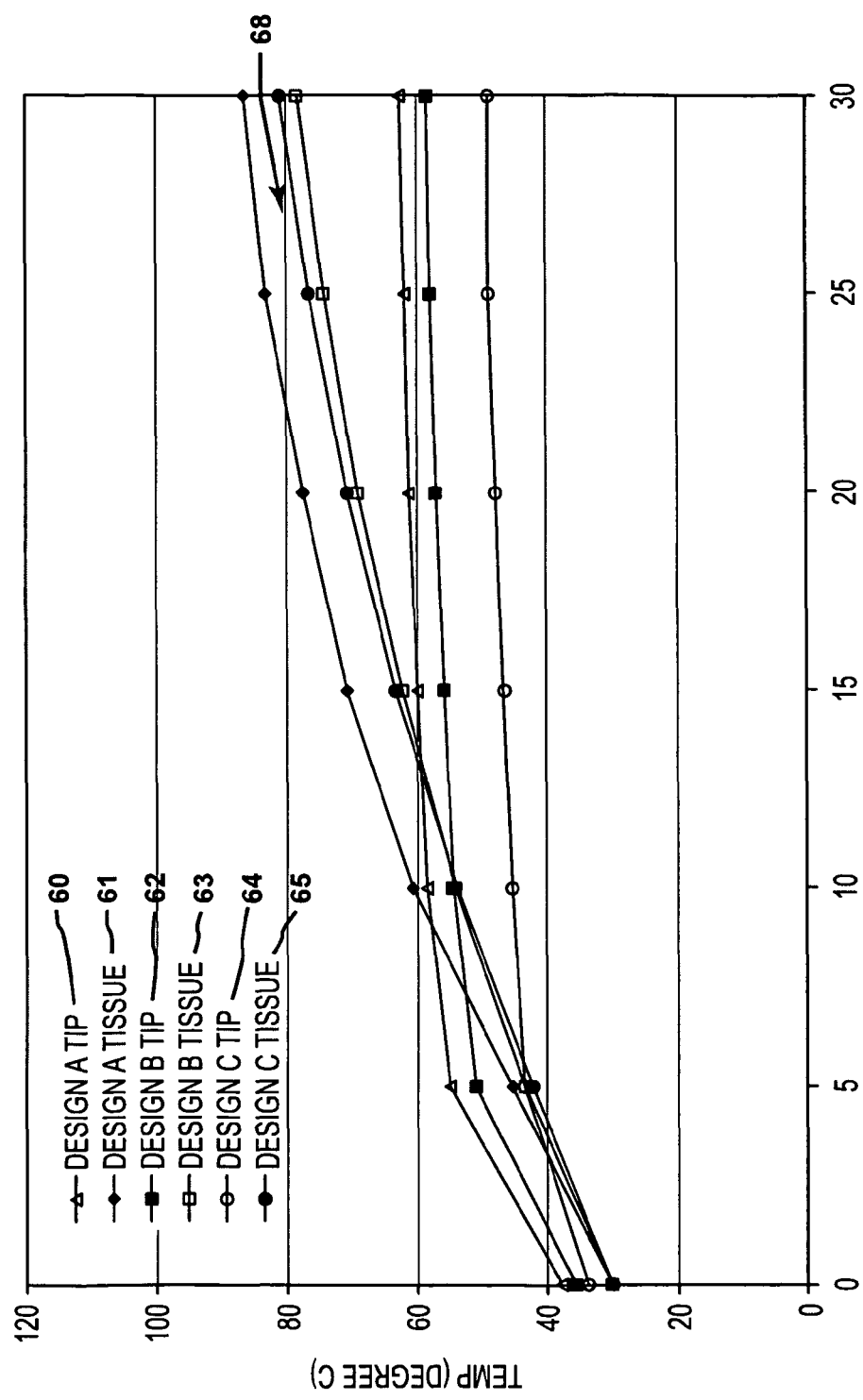
Figure 11:
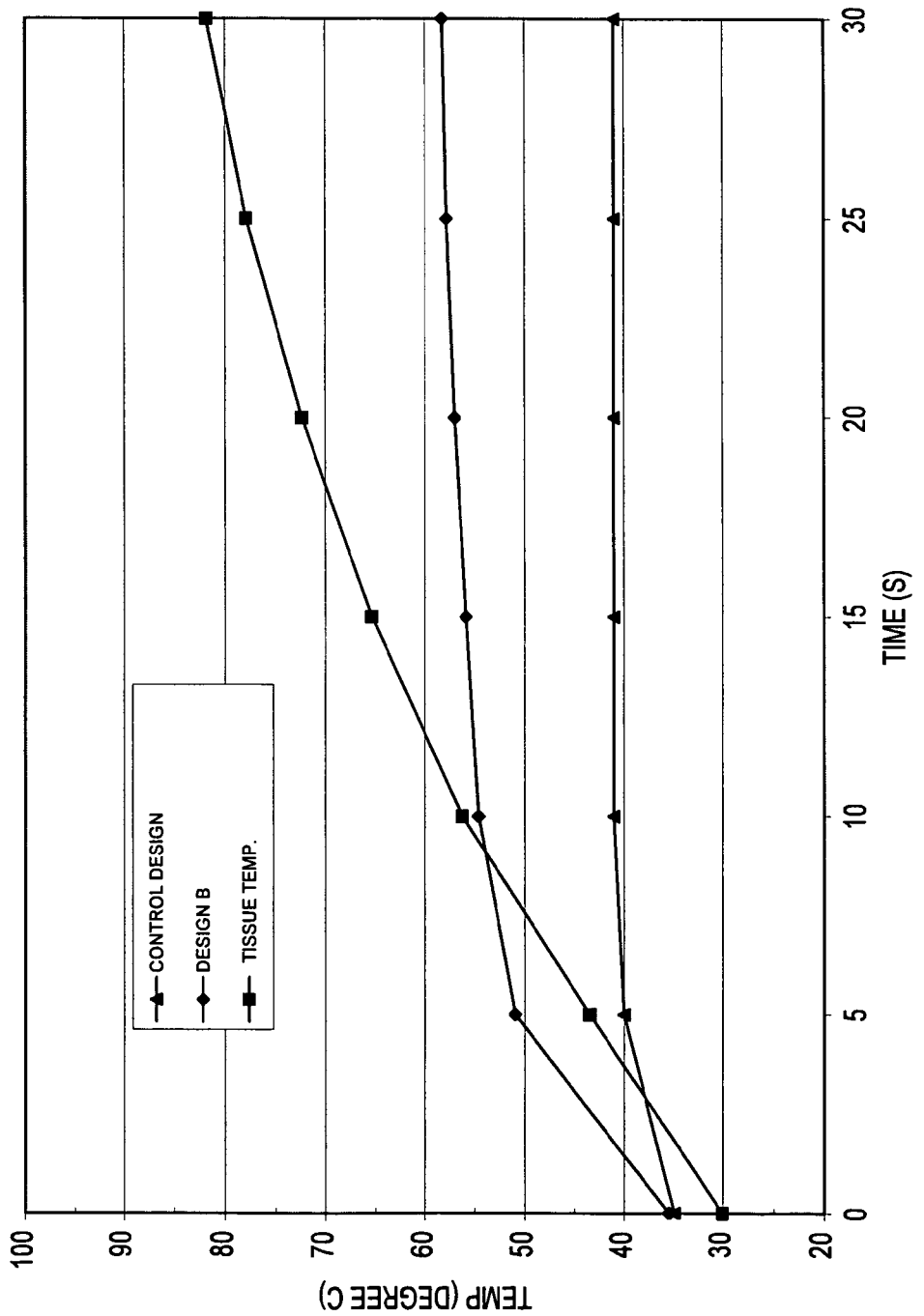

The results of the experiments are shown in FIGS. 9, 10 and 11. FIG. 9 shows only the temperature of the distal member of the Designs A 60, B 62, C 64 and the Control 66. As seen from FIG. 9, the temperature of the Control 66, non-insulated ablation electrode assembly resulted in the largest temperature measurement disparity, lowering the measured temperature from the 80 degrees Celsius operating temperature 68, to approximately 41 degrees Celsius. This substantial difference in temperature represents the difficulties in monitoring and controlling the ablation process that is commonly associated with non-insulated designs. Design C 64 succeeded in decreasing the temperature disparity approximately 8 degrees Celsius over the non-insulated design 66. Designs A 60 and B 62, however, provided significantly improved reduction of the temperature disparity to approximately 62 degrees Celsius and 58 degrees Celsius, respectively. The difference in temperature disparity between Designs A 60 and B 62 and C 64 and the Control 66 represent significant benefits for controlling and monitoring ablation procedures.

FIG. 10 shows the results of a second experiment measuring the temperature of the distal member and also the measured temperature of the corresponding tissue 61, 63, 65, respectively, being tested. Again, Designs A 60 and B 62 resulted in a much closer disparity between the actual tissue temperatures 61, 63 and distal member as compared to Design C 64. This further substantiates the structural advantages of the embodiments of the present invention compared to known insulated and non-insulated irrigated ablation electrode assemblies.

FIG. 11 identifies the measured temperature of the tissue and compares Design B to the Control design under the same test conditions. Again, as shown in FIG. 11, the temperature of the non-insulated tip of the Control design was significantly lower than the insulated tip of Design B.

Other embodiments and uses of the devices and methods of the present invention will be apparent to those skilled in the art from consideration of the specification and practice of the invention disclosed herein. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for improved measurement and control of a temperature of an irrigated ablation electrode assembly or a target site and minimization of coagulation and excess tissue damage at and around the target site comprising the steps of:
   providing the irrigated ablation electrode assembly having at least one temperature sensor disposed within a distal member of the irrigated ablation electrode assembly and having a proximal member separate from the distal member, wherein the irrigated ablation electrode assembly includes an ablation electrode;
   providing an irrigation pathway within the proximal member for delivery of a fluid to an external portion of the ablation electrode and the target site to minimize excess tissue damage during operation of the ablation electrode; and
   providing a poor thermally conductive material between the irrigation pathway and the distal member to reduce a thermal effect of the fluid on measurement of the temperature of the distal member during operation of the ablation electrode and during delivery of the fluid to the target site, wherein the poor thermally conductive material defines a lumen through which an operable connection of the temperature sensor is disposed.

2. The method of claim 1 further comprising the step of providing a second poor thermally conductive material disposed between the irrigation pathway and the distal member.

3. The method of claim 1 further comprising the step of providing a thermally conductive material between the at least one temperature sensor and the distal member.

4. The method of claim 1 wherein providing the irrigated ablation electrode assembly comprises providing an electrically conductive distal member having a first end and a second end.

5. The method of claim 4 wherein the electrically conductive distal member is fabricated from a material selected from the group comprising platinum, gold, iridium, stainless steel, palladium or mixtures thereof.

6. The method of claim 4 wherein providing the irrigation pathway comprises providing the irrigation pathway such that the irrigation pathway extends radially from a central axis of the irrigated ablation electrode assembly toward an outer portion of the proximal member to an outlet.

7. The method of claim 6 further comprising disposing the distal member and the proximal member such that one of the first end or the second end of the distal member is configured to receive only a portion of the proximal member such that the portion of the proximal member is disposed internally relative to the distal member.

8. The method of claim 7 wherein providing the irrigation pathway comprises separating the irrigation pathway and the outlet longitudinally from the distal member and the at least one temperature sensor.

9. The method of claim 1 wherein providing the irrigation pathway comprises providing the irrigation pathway such that the irrigation pathway extends at an angle perpendicular to a horizontal axis of the proximal member.

10. The method of claim 1 wherein providing the irrigation pathway comprises providing the irrigation pathway such that the irrigation pathway extends axially towards the distal member at an angle substantially less than perpendicular to a horizontal axis of the proximal member.

11. The method of claim 10 wherein providing the irrigation pathway comprises providing the irrigation pathway so as to extend axially towards the distal member at an angle between approximately 20 and approximately 70 degrees from an angle perpendicular to the horizontal axis of the proximal member.

12. The method of claim 1, wherein:
the distal member is formed from a first type of material; and
the poor thermally conductive material is formed from a second type of material, different from the first type of material.

13. A method for improved measurement and control of a temperature of an irrigated ablation electrode assembly, the method comprising:
providing the ablation electrode assembly having at least one temperature sensor disposed within a first member of the irrigated electrode assembly and having a second member separate from the first member, wherein the irrigated ablation electrode assembly includes an ablation electrode;
providing an irrigation pathway within the second member for delivery of a fluid to an external portion of the ablation electrode and a target site during operation of the ablation electrode; and
providing a poor thermally conductive material between the irrigation pathway and the first member to reduce a thermal effect of the fluid on measurement of the temperature of the first member during operation of the ablation electrode and during delivery of the fluid, wherein the poor thermally conductive material defines a lumen through which an operable connection of the temperature sensor is disposed.

14. The method of claim 13 wherein the first member comprises a distal member and the second member comprises a proximal member.

15. The method of claim 13, wherein:
the first member is formed from a first type of material; and
the poor thermally conductive material is formed from a second type of material, different from the first type of material.

* * * * *